United States Patent
Sanborn

(10) Patent No.: US 9,562,028 B2
(45) Date of Patent: Feb. 7, 2017

(54) PROCESS FOR MAKING 2,5-FURANDICARBOXYLIC ACID

(71) Applicant: ARCHER DANIELS MIDLAND COMPANY, Decatur, IL (US)

(72) Inventor: Alexandra Sanborn, Lincoln, IL (US)

(73) Assignee: Archer Daniels Midland Co., Decatur, IL (US)

( * ) Notice: Subject to any disclaimer, the term of this patent is extended or adjusted under 35 U.S.C. 154(b) by 0 days.

(21) Appl. No.: 14/771,832

(22) PCT Filed: Mar. 5, 2014

(86) PCT No.: PCT/US2014/020482
§ 371 (c)(1),
(2) Date: Sep. 1, 2015

(87) PCT Pub. No.: WO2014/158838
PCT Pub. Date: Oct. 2, 2014

(65) Prior Publication Data
US 2016/0016926 A1    Jan. 21, 2016

Related U.S. Application Data

(60) Provisional application No. 61/782,589, filed on Mar. 14, 2013.

(51) Int. Cl.
C07D 307/68    (2006.01)
C07D 307/46    (2006.01)
C07D 307/71    (2006.01)

(52) U.S. Cl.
CPC .......... *C07D 307/68* (2013.01); *C07D 307/46* (2013.01); *C07D 307/71* (2013.01)

(58) Field of Classification Search
CPC .... C07D 307/68; C07D 307/46; C07D 307/71
See application file for complete search history.

(56) References Cited

FOREIGN PATENT DOCUMENTS

WO    WO 2013033058 A1 *   3/2013    ............ B01J 27/128

OTHER PUBLICATIONS

Van Putten, R-J., "Hydroxymethylfurfural, a versatile platform chemical made from renewable resources." Chemical reviews 113.3 (2013): 1499-1597.*

* cited by examiner

*Primary Examiner* — Samantha Shterengarts
*Assistant Examiner* — Matt Mauro
(74) *Attorney, Agent, or Firm* — William B. Miller

(57) ABSTRACT

A process is described for converting HMF to FDCA, comprising dissolving a quantity of HMF in water to form an aqueous solution including HMF, combining the aqueous solution including HMF with an oxygen source in the presence of a homogeneous metal salt catalyst, but in the substantial absence of any solvent for the HMF and the homogeneous metal salt catalyst other than water, and under conditions which are effective for oxidizing HMF in the presence of the catalyst to form FDCA, and then recovering an FDCA precipitate.

4 Claims, No Drawings

PROCESS FOR MAKING 2,5-FURANDICARBOXYLIC ACID

BACKGROUND OF THE INVENTION

The use of natural products as starting materials for the manufacture of various large-scale chemical and fuel products which are presently made from petroleum- or fossil fuel-based starting materials, or for the manufacture of biobased equivalents or analogs thereto, has been an area of increasing importance. For example, a great deal of research has been conducted into the conversion of natural products into fuels, as a cleaner and, certainly, as a more sustainable alternative to fossil-fuel based energy sources.

Agricultural raw materials such as starch, cellulose, sucrose or inulin are inexpensive and renewable starting materials for the manufacture of hexoses, such as glucose and fructose. It has long been appreciated in turn that glucose and other hexoses, in particular fructose, may be converted into other useful materials, such as 2-hydroxymethyl-8-furfuraldehyde, also known as 5-hydroxymethylfurfural or simply hydroxymethylfurfural (HMF):

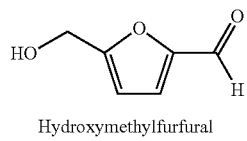

Hydroxymethylfurfural

The sheer abundance of biomass carbohydrates available provides a strong renewable resource base for the development of commodity chemical and fuel products based on HMF. For example, U.S. Pat. No. 7,385,081, issued in June 2008 to Gong, estimates, for example, that of the approximately 200 billion tons of biomass produced annually, 95% was in the form of carbohydrates, and only 3 to 4% of the total carbohydrates were then used for food and other purposes.

In view of this fact, and due to HMF's various functionalities, it has been proposed that the HMF thus obtainable from hexoses such as fructose and glucose, could be utilized to produce a wide range of products derived from renewable resources, such as polymers, solvents, surfactants, pharmaceuticals, and plant protection agents. HMF has in this regard been proposed, as either a starting material or intermediate, in the synthesis of a wide variety of compounds, such as furfuryl dialcohols, dialdehydes, esters, ethers, halides and carboxylic acids.

A number of the products discussed in the literature derive from the oxidation of HMF. Included are hydroxymethylfurancarboxylic acid (HMFCA), formylfurancarboxylic acid (FFCA), 2,5-furandicarboxylic acid (FDCA, also known as dehydromucic acid), and diformylfuran (DFF). Of these, FDCA has been discussed as a biobased, renewable substitute in the production of such multi-megaton polyester polymers as polyethylene terephthalate) or poly(butylene terephthalate). Derivatives such as FDCA can be made from 2,5-dihydroxymethylfuran and 2,5-bis(hydroxymethyl)tetrahydrofuran and used to make polyester polymers. FDCA esters have also recently been evaluated as replacements for phthalate plasticizers for PVC, see, e.g., WO 2011/023491A1 and WO 2011/023590A1, both assigned to Evonik Oxeno GmbH, as well as R. D. Sanderson et al., Journal of Appl. Pol. Sci. 1994, vol. 53, pp. 1785-1793.

While FDCA and its derivatives have attracted a great deal of recent commercial interest, with FDCA being identified, for instance, by the United States Department of Energy in a 2004 study as one of 12 priority chemicals for establishing the "green" chemical industry of the future, the potential of FDCA (due to its structural similarity to terephthalic add) to be used in making polyesters has been recognized at least as early as 1946, see GB 621,971 to Drewitt et al, "Improvements in Polymer".

Unfortunately, while HMF and its oxidation-based derivatives such as FDCA have thus long been considered as promising biobased starting materials, intermediates and final products for a variety of applications, viable commercial-scale processes have proven elusive. Acid-based dehydration methods have long been known for making HMF, being used at least as of 1895 to prepare HMF from levulose (Dull, Chem. Ztg., 19, 216) and from sucrose (Kiermayer, Chem. Ztg., 19, 1003). However, these initial syntheses were not practical methods for producing HMF due to low conversion of the starting material to product. Inexpensive inorganic acids such as $H_2SO_4$, $H_3PO_4$, and HCl have been used, but these are used in solution and are difficult to recycle. In order to avoid the regeneration and disposal problems, solid sulfonic acid catalysts have also been used. The solid acid resins have not proven entirely successful as alternatives, however, because of the formation of deactivating humin polymers on the surface of the resins.

In the acid-based dehydration methods, additional complications arise from the rehydration of HMF, which yields by-products such as levulinic and formic acids. Another unwanted side reaction includes the polymerization of HMF and/or fructose resulting in humin polymers, which are solid waste products and act as catalyst poisons where solid acid resin catalysts are employed, as just mentioned. Further complications may arise as a result of solvent selection. Water is easy to dispose of and dissolves fructose, but unfortunately, low selectivity and the formation of polymers and humin increases under aqueous conditions.

The realization of an economical commercial production of HMF has also been hindered by HMF's comparative instability and tendency to degrade. One approach that has been considered has been to either form more stable and easily separated HMF derivatives, for example, HMF ester and ether derivatives, or to quickly remove the HMF from exposure to those conditions, for example, acidic conditions, tending to contribute to its degradation.

An example of the former approach may be found in US 2009/0156841 by Sanborn et al., in which a method is provided of producing substantially pure HMF and HMF esters from a carbohydrate source by contacting the carbohydrate source with a solid phase catalyst; "substantially pure" was defined as referencing a purity of HMF of about 70% or greater, optionally about 80% or greater, or about 90% or greater.

An example of the latter approach may be found in WO 2009/012445 by Dignan et al., wherein HMF is proposed to be made by mixing or agitating an aqueous solution of fructose and inorganic acid catalyst with a water immiscible organic solvent to form an emulsion of the aqueous and organic phases, then heating the emulsion in a flow-through reactor at elevated pressures and allowing the aqueous and organic phases to phase separate. HMF is present in the aqueous and organic phases in about equal amounts, and is removed from both, for example, by vacuum evaporation and vacuum distillation from the organic phase and by passing the aqueous phase through an ion-exchange resin. Residual fructose stays with the aqueous phase. High fructose levels are advocated for the initial aqueous phase, to use relatively smaller amounts of solvent in relation to the amount of fructose reacted.

In commonly-assigned Patent Cooperation Treaty Application No. PCT/US12/66708 for "Process for Making HMF and HMF Derivatives From Sugars, With Recovery of Unreacted Sugars Suitable for Direct Fermentation to Ethanol", now published as WO 2013106136 ("WO '136"), we described a process for making HMF or HMF derivatives (e.g., the ester or ether derivatives) from an aqueous hexose sugar solution in which, according to certain embodiments, the acid-catalyzed dehydration step is conducted with rapid heating of the aqueous hexose solution from an ambient to a reaction temperature, as well as with rapid cooling of the HMF and/or HMF derivative unconverted sugar mixture prior to the separation of a fermentation-ready residual sugars product from the HMF and/or HMF derivative product. In addition, the time between when the aqueous hexose solution has been introduced into a reactor and the HMF and/or HMF ether products begin to be cooled is preferably limited.

By accepting limited per-pass conversion to HMF, the overall exposure of the HMF that is formed from any given aqueous hexose solution to acidic, elevated temperature conditions is limited, and preferably little to no unwanted or unusable byproducts such as humins are produced requiring waste treatments. Separation and recovery of the products is simplified and levels of HMF and other hexose dehydration products known to inhibit ethanol production by fermentation are reduced in the residual sugars product to an extent whereby the residual sugars product can be used directly for ethanol fermentation if desired. Processes conducted as described were characterized by very high sugar accountabilities and high conversion efficiencies, with very low losses of sugars being apparent.

Even more recently, in commonly-assigned Patent Cooperation Treaty Application Serial No. PCT/US2014/18186 for "Process For Making HMF From Sugars With Reduced Byproduct Formation, And Improved Stability HMF Compositions" (the "WO '186 Application"), further improvements are offered for addressing some of the difficulties that have been encountered in seeking to manufacture HMF on a commercial scale, especially from common hexose sugars from corn wet or dry milling or from the cellulosic fraction of a lignocellulosic biomass, for example. In particular, while WO '136 concerns limiting the exposure of HMF to acidic, elevated temperature conditions, we found in the WO '186 Application that oxidation, including especially autoxidation, of HMF also plays a heretofore unappreciated role in its degradation. Consequently, in the WO '186 Application, various processes are contemplated wherein one or more hexose sugars are dehydrated in a reduced oxygen environment with reduced degradation of the desired HMF product/feedstock for making FDCA or other oxidation products from HMF. As an example, in one embodiment, an HMF production process according to WO '136 can be conducted in a reduced oxygen environment, before the HMF (or HMF derivative) is used as a feedstock to an oxidation process for making FDCA.

In this regard, notwithstanding the numerous challenges confronting those seeking a commercially viable process for making HMF—so that large-scale production of a suitable HMF feedstock has not so far been realized—nevertheless, in recognition of the commercial interest in FDCA, a number of processes for making FDCA from HMF have been described in the technical and patent literature.

Several references describe processes for the oxidation of HMF or derivatives of HMF in a Mid-Century type process or a somewhat modified Mid-Century type process, see, for example, US Patent Application Publications No. 2012/0059178 A1 to Sanborn and 2012/0271060 to Muñoz de Diego et al. (with a number of like earlier references being described in each of these publications).

Patent Cooperation Treaty Application No. PCT/US2012/052800 for "Spray Oxidation Process for Producing 2,5-Furandicarboxylic Acid from Hydroxymethylfurfural", now published as WO 2013033058 ("WO '058"), is illustrative as well in describing the use of the Mid-Century, homogeneous Co/Mn/Br catalyst for oxidizing HMF to FDCA in a spray Oxidation process, but is notable also for the discovery that in the context of that spray oxidation process a crude dehydration product mixture from a conventional acid dehydration could be directly solubilized in a solvent for the catalyst (acetic acid being preferred), sprayed into the reactor and oxidized with subsequent recovery of the FDCA product in an unexpectedly high yield. Consequently an integrated, seamless process is contemplated wherein the HMF need not be isolated, purified or derivatized to prevent its degradation prior to its conversion to FDCA by oxidation, though as noted above in US 2009/0158841 by Sanborn et al, the acetate ester derivatives of HMF (formed in situ from combination With the acetic acid solvent) are readily oxidized to yield FDCA in the presence of the CoMnBr catalysts.

While the discoveries of WO '136, WO '186 and WO '058 thus can be seen individually and/or in combination to provide significant improvements in dealing with one long-standing impediment to the commercial realization of processes for making HMF and for making the HMF oxidation product FDCA—namely, the instability and tendency of HMF to degrade—nevertheless all of the Mid-Century type processes, however, use an organic solvent of some kind, that must (given the amounts used) be recovered and recycled; the use, recovery and recycle of an organic solvent such as acetic acid adds significant cost to the overall process.

Other processes have been proposed for converting HMF to FDCA, including processes using different heterogeneous catalysts for the oxidation of HMF to FDCA, but these various heterogeneously catalyzed methods also have their drawbacks—for example, long reaction times for reasonable conversions and yields, very dilute substrate concentrations, high catalyst-to-substrate ratios, a high content of expensive metals such as gold and platinum, difficulty in recovering the costly metal for reuse, generation of significant waste in working up the catalyst, difficulty in separation of FDCA from the heterogeneous catalyst and so forth.

It would consequently be highly desirable if a process Were available wherein a much less costly metal catalyst could be used for homogeneously catalyzing the oxidation of HMF to FDCA in water alone, whereby the expense associated with the use, recovery and recycle of an organic solvent in the previously known, homogeneously catalyzed Mid-Century type processes could be avoided along with the aforementioned drawbacks of the heterogeneously catalyzed methods.

SUMMARY OF THE INVENTION

The present invention accordingly in one aspect concerns a process for converting HMF to FDCA, wherein: a quantity of HMF is dissolved in water; the aqueous solution containing HMF is combined with an oxygen source in the presence of a homogeneous, water-soluble metal salt catalyst and under conditions which are effective for oxidizing HMF to form FDCA in the presence of the catalyst, but in the substantial absence of any solvent other than water; and FDCA product is precipitated out and recovered.

In another aspect, the present invention concerns a process for converting an aqueous feed containing one or more six-carbon sugars to FDCA, wherein the aqueous feed is dehydrated to a crude dehydration product mixture in HMF in the presence of an acid catalyst, then the crude dehydration product mixture is combined with an oxygen source in the presence of a homogeneous, water-soluble metal salt catalyst and under conditions which are effective for oxidizing HMF to form FDCA in the presence of the catalyst, but in the substantial absence of any solvent other than water; and FDCA product so formed is precipitated out and recovered. In certain embodiments, the homogeneous metal salt catalyst is a cobalt bromide catalyst.

DETAILED DESCRIPTION OF PREFERRED EMBODIMENTS

A preferred process of the present invention according to either aspect includes oxidizing HMF in water in the presence of a homogeneous metal salt catalyst which is solubilized in the water, then separating out the poorly water-soluble FDCA product from the catalyst by precipitation followed by filtration.

In general, the HMF and metal salt catalyst may be combined in water in any particular order, without limitation. Thus, for example, the catalyst may be added to an aqueous solution of HMF. This will be the most convenient means of making the combination in an integrated process according to the second aspect, wherein a preceding acid-catalyzed dehydration step is employed for converting an aqueous feed containing one or more six-carbon sugars to a crude dehydration product mixture including HMF. The preceding acid-catalyzed dehydration step can be carried out by any of the methods which have been referenced and described above or by any other known method for carrying out this transformation, but preferred methods will employ a solid acid catalyst and/or be carried out using the teachings of our WO '136 or WO '186 filings, in order to produce a crude dehydration product mixture while reducing exposure of the HMF therein to conditions (including acidic conditions and especially acidic conditions at elevated temperatures, as well as oxygen (as shown by WO '186) prior to the subsequent oxidation step) that may contribute to the degradation of HMF prior to its conversion to FDCA by the subsequent oxidation step.

In other embodiments, for example, wherein the HMF has been previously, separately produced and/or wherein an intermediate HMF purification or isolation step is used in an integrated process after an acid-catalyzed dehydration step, the HMF and metal salt catalyst may be concurrently solubilized in water: such an embodiment will be understood as consistent with the summary process steps related above. In another embodiment, the HMF is added to water in which the metal salt catalyst has already been solubilized.

The oxygen source may be any material that will contribute oxygen for oxidizing the HMF to form oxidation products of HMF inclusive of FDCA, for example, air, oxygen-enriched air or oxygen. The oxygen source can be bubbled into the aqueous solution containing the HMF and metal salt catalyst, or as shown in the example below, may be added to a reactor containing the aqueous solution as a pressurized gas.

The concentration of HMF in the aqueous solution need not be limited, as in the practice of the heterogeneously catalyzed processes, to maintain a low FDCA concentration in the aqueous solution and prevent the FDCA product from precipitating out, thereby complicating separation from the heterogeneous catalyst. As well, no base is needed in order for such higher HMF feed concentrations to be used in order to form the more readily soluble carboxylate salts of FDCA, since the process of the present invention takes advantage of the poorly water-soluble nature of the ultimately desired FDCA product to separate the FDCA product from the metal salt catalyst still remaining in the aqueous solution.

A variety of metal salt catalysts may be used, for example, the water-soluble salts of cobalt, manganese, cerium and zirconium, especially the acetate, carbonate and halide (and particularly bromide) salts of these metals. A preferred catalyst is cobalt bromide. The cobalt bromide catalyst is considerably less costly than the heterogeneous platinum, gold and ruthenium catalysts of the several references summarized above, and as a homogeneous catalyst is more readily available to the reactants, enabling a much reduced catalyst-to-substrate ratio to be used with reasonable reaction times to achieve an acceptable conversion of the HMF reactant and at least a certain acceptable yield of the desired FDCA product.

Typically, the reaction temperature will be from 80 to 180 degrees Celsius, using oxygen to pressurize the reactor to from 2.1 MPa, gauge (300 psi) to 6.9 MPa, gauge (1000 psig), or using corresponding pressures of oxygen-enriched air or air to provide an equivalent supply of oxygen for the reaction. At a cobalt bromide content of from 0.1 to 1.0 molar percent (relative to the HMF substrate), reaction times on the order of from 1 hour to 10 hours can be expected to provide a yield of at least 30 percent of FDCA. Preferably, with optimization, yields of at least 35 percent of FDCA be realized, and more preferably, at least 40 percent. Quantitative to near-quantitative conversion of the HMF is expected, with good to excellent catalyst life.

The present invention is further illustrated by the following, non-limiting example:

Example 1

Distilled HMF (5 grams, 92% purity) was introduced into a 100 mL MC Series, stainless steel stirred reactor vessel (Pressure Products Industries, Warmister Pa.), and cobalt (II) bromide dehydrate (28.8 mg) and water (50 grams) were added. The reactor was charged with oxygen to MPa (300 psi) and increased to 4.6 MPa (650 psi) after 50 minutes. The temperature increased from ambient temperature to reaction temperature of 100° C. and after 0.5 hours at 100° C., the reaction temperature was increased from 100 to 115° C. The temperature was maintained at about 115-117° C. and an oxygen pressure of 4.2 MPa (600 psi) for an additional 1.5 hours, at which time the reaction mixture was allowed to cool and the reaction remained under oxygen atmosphere at ambient temperature for 15 hours. Samples were pulled regularly with the solids separated (retained) by vacuum filtration. Conversion of the HMF was confirmed by gas chromatography/mass spectroscopy, high performance liquid chromatography and/or $^1$H nuclear magnetic resonance. The solid that precipitated out was identified by GC/FID as essentially pure FDCA.

What is claimed is:
1. A process for converting HMF to FDCA, comprising:
providing an aqueous solution comprising HMF;

combining the aqueous solution comprising HMF with an oxygen source in the presence of a homogeneous metal salt catalyst, but in the absence of any solvent for the HMF and the homogeneous metal salt catalyst other than water, and under conditions which are effective for oxidizing HMF in the presence of the catalyst to form FDCA; and recovering an FDCA precipitate.

2. The process according to claim 1, wherein the homogeneous metal salt catalyst is selected from the group consisting of the acetate, carbonate and halide salts of any of cobalt, manganese, cerium and zirconium.

3. The process according to claim 2, wherein the catalyst is cobalt bromide.

4. The process according to claim 1, wherein the aqueous solution comprising HMF is provided and combined with the oxygen source in the presence of the homogeneous metal salt catalyst by:

dehydrating an aqueous feed including one or more six-carbon sugars in the presence of an acid catalyst to yield a crude dehydration product mixture comprising HMF;

combining the crude dehydration product mixture with a homogeneous metal salt catalyst; and directly supplying the crude dehydration product mixture with the homogeneous metal salt catalyst as the aqueous solution to the oxidation step.

* * * * *